US007217295B2

(12) United States Patent
Samain et al.

(10) Patent No.: US 7,217,295 B2
(45) Date of Patent: May 15, 2007

(54) USE OF SOLUBLE CONDUCTIVE POLYMERS FOR TREATING HUMAN KERATIN FIBERS

(75) Inventors: Henri Samain, Bievres (FR); Grégory Plos, Paris (FR); Nathalie Mougin, Paris (FR)

(73) Assignee: L'Oreal S.A., Paris (FR)

( * ) Notice: Subject to any disclaimer, the term of this patent is extended or adjusted under 35 U.S.C. 154(b) by 292 days.

(21) Appl. No.: 10/355,227

(22) Filed: Jan. 31, 2003

(65) Prior Publication Data
US 2004/0103486 A1 Jun. 3, 2004

Related U.S. Application Data

(60) Provisional application No. 60/353,991, filed on Feb. 5, 2002.

(30) Foreign Application Priority Data
Jan. 31, 2002 (FR) .................. 02 01144

(51) Int. Cl.
*A61K 7/13* (2006.01)
(52) U.S. Cl. ............. 8/405; 8/406; 8/435; 8/575; 549/59; 549/71; 549/79; 549/83
(58) Field of Classification Search ............ 8/405, 8/406, 435, 575; 549/59, 71, 79, 83
See application file for complete search history.

(56) References Cited

U.S. PATENT DOCUMENTS

| 2,528,378 | A | 10/1950 | McCabe, Jr. et al. .... 265/309.6 |
| 2,781,354 | A | 2/1957 | MCabe, Jr. et al. ...... 260/309.6 |
| 3,158,542 | A | 11/1964 | Kalopissis ................. 167/88 |
| 3,723,325 | A | 3/1973 | Parran ..................... 252/106 |
| 5,288,494 | A | 2/1994 | Yoshihara et al. .......... 424/401 |
| 5,338,540 | A | 8/1994 | Lee et al. |
| 5,449,519 | A | 9/1995 | Wolf et al. ................ 424/401 |
| 5,569,708 | A | 10/1996 | Wudl et al. |
| 5,616,150 | A | 4/1997 | Moeller et al. .............. 8/405 |
| 5,755,829 | A | 5/1998 | Terranova et al. |
| 5,830,446 | A | 11/1998 | Berthiaume et al. ....... 424/70.1 |
| 5,863,981 | A | 1/1999 | Wudl et al. |
| 5,891,968 | A | 4/1999 | Wudl et al. |
| 6,042,620 | A | 3/2000 | Braun et al. ................ 8/410 |
| 6,132,475 | A | 10/2000 | Chassot et al. .............. 8/409 |
| 6,203,580 | B1 | 3/2001 | Vandenbossche et al. ...... 8/421 |
| 6,242,561 | B1* | 6/2001 | Mohwald et al. ........... 528/377 |
| 2002/0146442 | A1 | 10/2002 | Sendelbach et al. ........ 424/401 |
| 2003/0041391 | A1 | 3/2003 | Rozzell et al. .............. 8/401 |
| 2004/0103486 | A1 | 6/2004 | Samain et al. |
| 2004/0107512 | A1 | 6/2004 | Samain et al. ............... 8/405 |

FOREIGN PATENT DOCUMENTS

| DE | 196 31 563 | 2/1998 |
| DE | 299 02 262 | 5/1999 |
| DE | 100 08 305 | 6/2001 |
| DE | 101 05 139 | 8/2002 |
| EP | 0 539 123 | 4/1993 |
| EP | 0 540 448 | 5/1993 |
| EP | 0 861 835 | 9/1998 |
| EP | 0 943 614 | 9/1999 |
| EP | 1 228 749 | 9/2002 |
| FR | 2 709 954 | 3/1995 |
| FR | 2 825 619 | 12/2002 |
| FR | 2835182 | 9/2003 |
| FR | 2 850 568 | 8/2004 |
| GB | 2 307 639 | 6/1997 |
| JP | 55-065201 | 5/1980 |
| JP | A S61-183213 | 8/1986 |
| JP | A S61-278526 | 12/1986 |
| JP | 62-167771 | 7/1987 |
| JP | A S64-036609 | 7/1989 |
| JP | 3-294580 | 12/1991 |
| JP | 5-310597 | 11/1993 |
| JP | A 5-310822 | 11/1993 |
| JP | 06-100432 | 4/1994 |
| JP | A H07-238150 | 9/1995 |
| JP | A 9-120709 | 5/1997 |
| JP | 09-221408 | 8/1997 |
| JP | 11-291410 | 10/1999 |
| JP | A 2000-327837 | 11/2000 |
| WO | WO 94/24988 | 11/1994 |
| WO | WO 97/32914 | * 3/1997 |
| WO | WO 99/47570 | 9/1999 |
| WO | WO 02/47633 | 6/2002 |
| WO | WO 03/063809 | 8/2003 |
| WO | WO 04/066968 | 8/2004 |

OTHER PUBLICATIONS

STIC Search Report Dec. 5, 2005.*
STIC Search Report (Jul. 26, 2006).*
Porter, M.R., "Nonionics", Handbook of Surfactants, Chapter 7, 1991, pp. 116-178.
Porter, M.R., "Nonionics", Handbook of Surfactants, 2nd ed., Chapter 7, 1994, pp. 169-246.

(Continued)

Primary Examiner—Eisa Elhilo
(74) Attorney, Agent, or Firm—Finnegan, Henderson, Farabow, Garrett & Dunner, L.L.P

(57) ABSTRACT

The invention relates to the use of a composition comprising at least one conductive polymer in a cosmetically acceptable medium, said polymer being in soluble form in said medium, as, or for the manufacture of, cosmetic products for giving a visual effect to human keratin fibers and more particularly the hair, and also, when said conductive polymer absorbs in the visible region, as, or for the manufacture of, cosmetic products intended to color said fibers.

The invention also relates to the corresponding treatment process.

18 Claims, No Drawings

OTHER PUBLICATIONS

Rasmussen, S.C., "A New, General Approach to Tuning the Properties of Functionalized Polythiophenes: The Oxidative Polymerization of Monosubstituted Bithiophenes," Chem. Mater., vol. 10, No. 7, 1998, pp. 1990-1999.

Rasmussen et al., "Highly Conjugated, Water-Soluble Polymers via the Direct Oxidative Polymerization of Monosubstituted Bithiophenes", Macromolecules, vol. 31, No. 3, Feb. 10, 1998, pp. 932-936.

Sotzing, G.A., "Redox Active Electrochromic Polymers from Low Oxidation Monomers Containing 3,4-Ethylenedioxythiophene (EDOT)," Synthetic Metals, vol. 84, 1997, pp. 199-201.

English language Derwent Abstract of non-English language DE 196 31 563 (attached to DE 196 31 563).

English language Derwent Abstract of non-English language DE 100 08 305 (attached to DE 100 08 305).

English language Derwent Abstract of non-English language FR 2 709 954 (attached to FR 2 709 954).

English language Derwent Abstract of non-English language FR 2 825 619 (attached to FR 2 825 619).

English language Derwent Abstract of non-English language FR 2 850 568 (attached to FR 2 850 568).

English language Derwent Abstract of non-English language JP 55-065201 (attached to JP 55-065201).

English language Derwent Abstract of non-English language JP 62-167771 (attached to JP 62-167771).

English language Derwent Abstract of non-English language JP 3-294580 (attached to JP 3-294580).

English language Derwent Abstract of non-English language JP 5-310597 (attached to JP 5-310597).

English language Derwent Abstract of non-English language JP 06-100432 (attached to JP 06-100432).

English language Derwent Abstract of non-English language JP 09-221408 (attached to JP 09-221408).

English language Derwent Abstract of non-English language JP 11-291410 (attached to JP 11-291410).

Examination Report of FR 2835181.

Examination Report of WO 03/063811.

Litvinov, V.P. et al., Infrared Absorption Spectra of Mono- and Diacylated Thiophene Homologs, Academy of Sciences of the USSR, No. 1, pp. 166-168, Jan. 1961.

Rasmussen, Seth C. et al., "A new, General approach to Tuning the Properties of Functionalized Polythlophenes: The Oxidative Polymerization of Monosubstituted Bithiophenes," Chem. Mater 1998, vol. 10, No. 7, 1999.

Co-pending U.S. Appl. No. 10/355,228, filed Jan. 31, 2003.

Office Action mailed Oct. 25, 2005 in Co-pending U.S. Appl. No. 10/355,228.

French Search Report for French Patent No. FR 2835182, priority document for U.S. Appl. No. 10/355,228.

English Language Abstract of JP-A 5-310822.

English Language Derwent Abstract of JP-A 2000-327837.

English Language Derwent Abstract of JP-A S64-036609.

English Language Derwent Abstract of JP-A S61-278526.

* cited by examiner

USE OF SOLUBLE CONDUCTIVE POLYMERS FOR TREATING HUMAN KERATIN FIBERS

This application claims the benefit of U.S. Provisional Application No. 60/353,991 filed Feb. 5, 2002.

The invention relates to the use of a composition comprising at least soluble one conductive polymer in a cosmetically acceptable medium, as, or for the manufacture of, cosmetic products for giving a visual effect to human keratin fibers and more particularly to the hair, and also, when said conductive polymer absorbs in the visible region, as, or for the manufacture of, cosmetic products intended to color said fibers.

The invention also relates to the corresponding treatment process.

Products for giving the hair sheen effects are known. Such products contain molecules, or even polymers, in dissolved, emulsified or dispersed form, in a cosmetic solvent.

However, these products still do not give the hair the desired sheen.

In order to obtain a sheen effect on the hair, it is known practice to use compositions that are rich in lubricant hydrophobic substances, such as organic oils or waxes or silicones. However, in this case also, the sheen effect obtained lacks intensity and generally gives the hair an artificial appearance.

In addition, such compositions, once applied to the hair, have the drawback of giving the hair a greasy or sticky feel, which is unsatisfactory.

There is thus a need to find cosmetic hair compositions capable of giving the hair in particular intense and natural sheen without having the drawbacks mentioned above.

In addition, in order to obtain particularly attractive effects, combining a visual effect such as the provision of sheen with the provision of coloration may occasionally prove to be advantageous.

Now, it has been found, entirely surprisingly and unexpectedly, and this forms the basis of the present invention, that it was possible to uniformly give to the entire head of hair in particular a sheen that is substantially more intense, more natural and more attractive than that given with the prior art means, by using conductive polymers.

In addition, when said conductive polymers absorb in the visible spectrum, a visual effect, such as sheen and color, are simultaneously obtained.

Finally, the hair advantageously has a soft and pleasant feel.

A first subject of the present invention is thus the use of a composition comprising at least one conductive polymer in a cosmetically acceptable medium, said polymer being in soluble form in said medium, as an agent for giving a visual effect to human keratin material, preferably to human keratin fibers and more particularly to the hair.

A subject of the invention is also the use of a composition comprising at least one conductive polymer in a cosmetically acceptable medium, said polymer being in soluble form in said medium, for the manufacture of cosmetic products for giving a visual effect to human keratin material, preferably to human keratin fibers, and more particularly to the hair.

The invention also relates to a process for treating human keratin fibers, and more particularly hair, with a composition comprising said conductive polymers.

According to a first variant, the process consists in applying to the wet or dry fibers, the composition comprising at least one conductive polymer in a cosmetically acceptable medium, said polymer being in soluble form in said medium, and then in evaporating the medium or leaving the medium to evaporate at between 20 and 120° C., preferably between 20 and 80° C., until the fibers are dry.

According to a second variant, the process consists in applying to the wet or dry fibers, the composition comprising at least one conductive polymer in a cosmetically acceptable medium, said polymer being in soluble form in said medium, and then in rinsing said fibers and drying them at between 20 and 120° C.

A subject of the invention is a composition for dyeing human keratin fibers and more particularly the hair, comprising an effective amount of at least one conductive polymer that absorbs in the visible spectrum, in a cosmetically acceptable medium, said polymer being in soluble form in said medium.

However, other characteristics and advantages of the invention will emerge more clearly on reading the description and the examples that follow.

For the purposes of the present invention, the term "visual effect" encompasses sheen, color, metallic, goniochromatic, shimmering, fluorescent, thermochromic and electrochromic effects.

Moreover, and more particularly, it should be noted that the sheen corresponds to the light intensity reflected at an angle $\alpha$ when the lock of hair is illuminated at an angle $-\alpha$. The angle $\alpha$ conventionally used for measuring this specular reflection, in other words sheen, is 20°. This provision of sheen may be measured by using a glossmeter, as described, for example, in ISO standard 2813-1994 of the AFNOR (August 1994, amended in February 1997).

Conductive Polymers

According to the present invention, the term "conductive polymer" means a molecular structure in which the monomer(s) show(s) high electronic delocalization and the arrangement of which in the polymer skeleton allows the $\pi$ orbitals to overlap. This chemical characteristic is reflected by a phenomenon of electrical conduction which may or may not be accompanied by a phenomenon of absorption in the UV-visible spectrum, or even in the infrared spectrum.

For the purposes of the present invention, the expression "conductive polymer that absorbs in the visible spectrum" means any conductive polymer that has a nonzero absorbance in the wavelength range from 400 to 800 nm even if the absorption maxima of the polymer are outside this range.

The conductive polymers used in the context of the present invention are conductive polymers that are soluble in the cosmetic medium that is suitable for the application. The polymer is said to be soluble in the medium when it forms a clear isotropic liquid at 25° C. in the medium comprising water or a water/solvent mixture; this is obtained throughout all or some of a concentration range of between 0.001% and 50% by weight of conductive polymer.

Furthermore, the polymers advantageously have a conductivity of between $10^{-5}$ and $5 \times 10^5$ siemens/cm, more particularly between $10^{-3}$ and $10^5$ siemens/cm and preferably between $10^{-1}$ and $10^4$ siemens/cm. The conductivity is measured using a current generator (RM2 Test Unit sold by the company Jandel) equipped with a four-point measuring head (Universal four-point probes sold by the company Jandel). The four aligned points separated by the same spacing d are applied by simple pressure to the sample to be analyzed. A current I is injected via the outer points using the current source, thus creating a variation in potential. The voltage U is measured between the two inner points connected to the voltmeter of the current generator.

In this configuration, the conductivity of the sample, expressed in S/cm, is given by the following expression:

$$\sigma = (K \times I)/(U \times e)$$

in which:
K is the coefficient dependent on the position of the contacts on the surface of the sample.

When the points are aligned and equidistant, K is equal to: $\Pi/\log(2)$
I: injected current value, expressed in amperes
U: measured voltage value, expressed in volts
e: sample thickness, expressed in cm.

This expression can be used only when the thickness of the material is negligible compared with the distance d existing between two points (e/d<0.25). To obtain thicknesses that are sufficiently small and thus to be able to calculate the conductivity of the material, it is recommended to perform the measurement on a nonconductive support (for example a glass slide) coated with the material to be analyzed obtained by evaporation of a dilute solution. In order to improve the homogeneity of the coating to be analyzed, it is also recommended to use the "spin-coating" deposition technique.

More particularly according to the invention, the conductive polymers that are preferably used are those which absorb in the visible spectrum and which are chosen in particular from the group formed by homopolymers and copolymers comprising:

the polyanilines of structure (I) below:

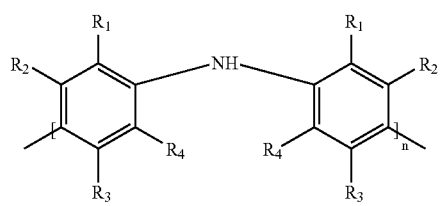

(I)

the polypyrroles of structure (IIa) and (IIb) below:

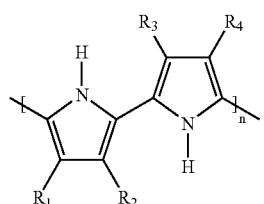

(IIa)

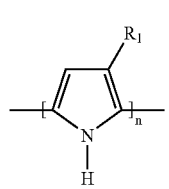

(IIb)

the polythiophenes of formulae (IIIa) and (IIIb) below:

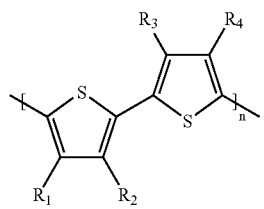

(IIIa)

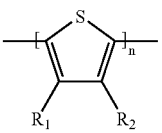

(IIIb)

the polythiophene vinylenes of formula (IIIbis) below:

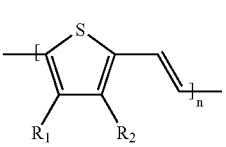

(IIIbis)

the polyfurans of formula (IV) below:

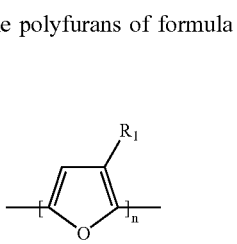

(IV)

the paraphenylene sulfides of structure (V) below:

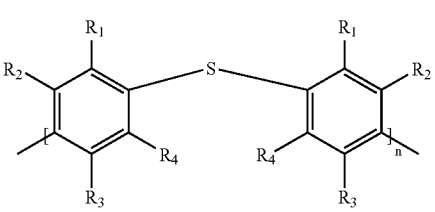

(V)

the poly-para-phenylene vinylenes of formula (VI) below:

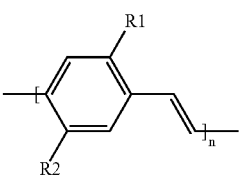

(VI)

the polyindoles of formulae (VII) below:

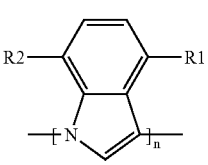

(VII)

the aromatic polyamides of formulae (VIIIa), (VIIIb), (VIIIc) and (VIIId) below:

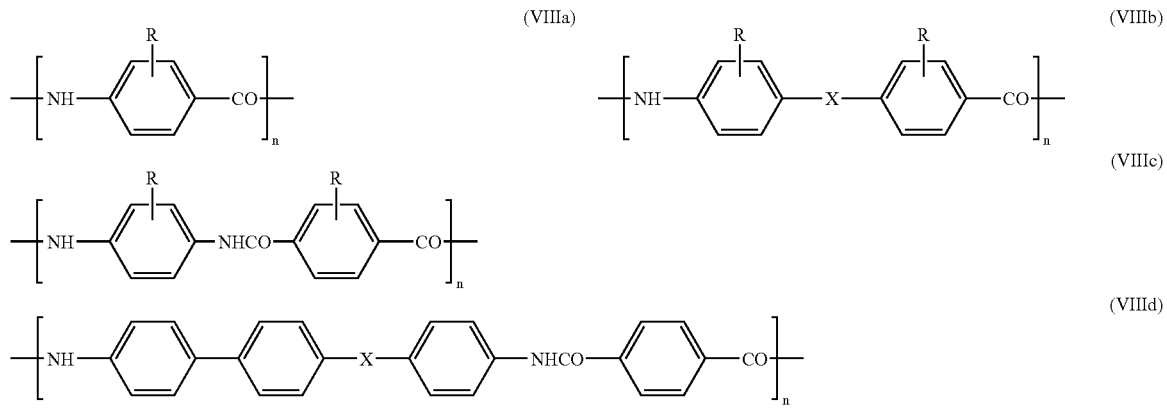

the aromatic polyhydrazides of formulae (IXa), (IXb) and (IXc) below:

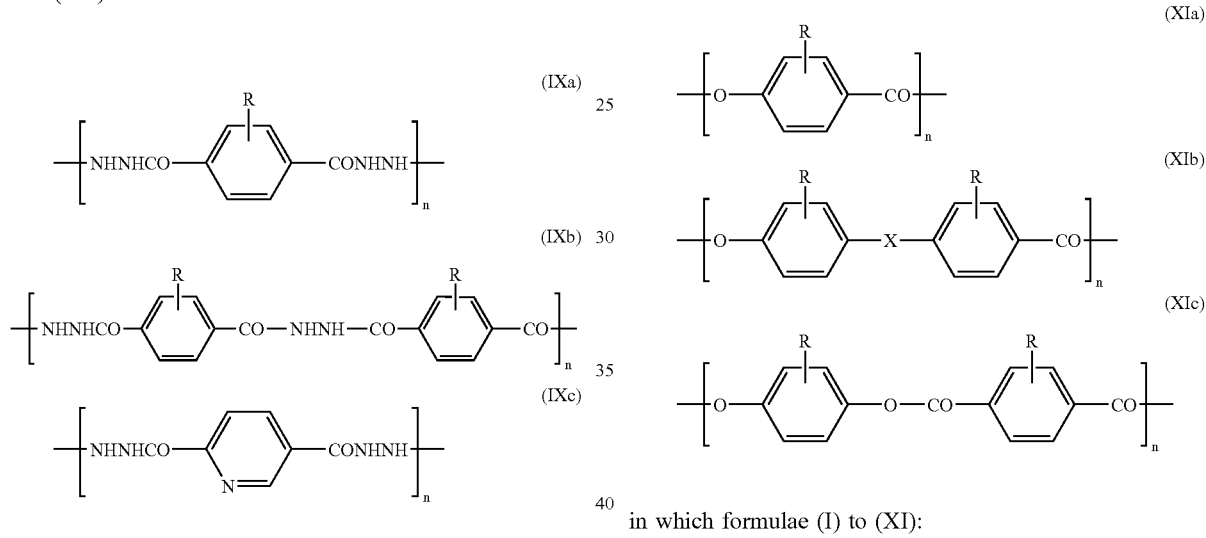

the aromatic polyazomethines of formulae (Xa), (Xb), and (Xc) below:

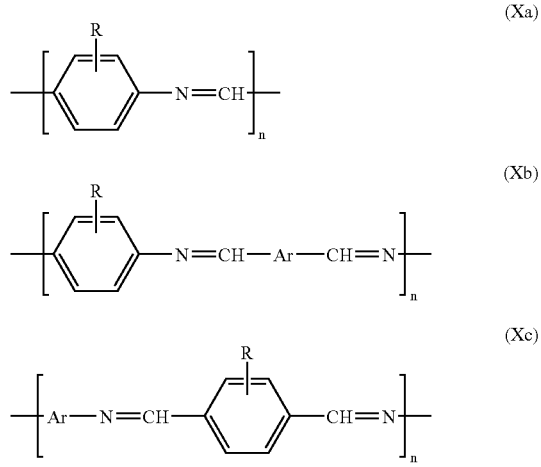

the aromatic polyesters of formulae (XIa), (XIb) and (XIc) below:

in which formulae (I) to (XI):

n ranges from 5 to 10 000, in particular from 5 to 1 000, more particularly from 10 to 1 000 and preferably from 20 to 700, the radicals R and $R_1$ to $R_4$, which may be identical or different, are chosen from the group formed by hydrogen, a radical —R', —OR', —COOR', and —OCOR', with R' representing a linear or branched $C_1$–$C_{20}$ alkyl radical, a halogen atom (preferably chosen from chlorine, bromine or iodine), a nitro radical, a cyano radical, an alkylcyano radical and solubilizing groups, it being understood that at least one radical from among R and $R_1$ to $R_4$ denotes a solubilizing group;

X=—NHCO—, —O—, —S—, —$SO_2$—, —N=N—, —C($CH_3$)$_2$—, —$CH_2$—, —CH=CH—, —CH=N—;

Ar represents a radical comprising a monoaromatic or polyaromatic radical.

More particularly, Ar represents at least one radical chosen from the following:

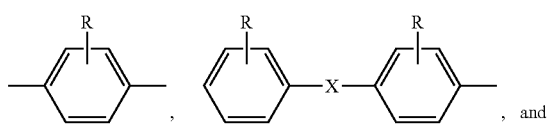

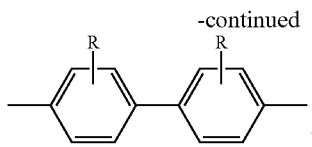

For the purposes of the present invention, the term "solubilizing group" means a group that solubilizes said molecule in the cosmetic medium such that the polymer has a conductive nature after drying the composition.

The solubilizing groups are preferably chosen from the group formed by:
- a carboxylic radical (—COOH) or carboxylate radical (—COO—M+ with M representing an alkali metal such as sodium or potassium, an alkaline-earth metal, an organic amine such as a primary, secondary or tertiary amine, an alkanolamine or an amino acid),
- a sulfonic radical (—SO$_3$H) or sulfonate radical (—SO$_3^{-M+}$, M having the same definition as above),
- a primary, secondary or tertiary amine radical,
- a quaternary ammonium radical such as —NR'$_3^+$Z$^-$ with Z=Br, Cl or (C$_1$–C$_4$)alkyl-OSO$_3$ and R' alkyl, which may be identical or different, C$_1$ to C$_{20}$ linear or branched, or two of them forming a heterocycle with the nitrogen,
- a hydroxyl radical,
- a C$_2$–C$_3$ polyalkene oxide radical.

The carboxylic or sulfonic acid functions may or may not be neutralized with a base, such as sodium hydroxide, 2-amino-2-methylpropanol, triethylamine or tributylamine.

The amine radicals may or may not be neutralized with a mineral acid, such as hydrochloric acid, or with an organic acid, such as acetic acid or lactic acid, for example.

In addition, it should be noted that said solubilizing radicals may be linked to the ring via a spacer group, for instance a radical —R"—, —OR"—, —OCOR"— or —COOR"— with R" representing a linear or branched C$_1$–C$_{20}$ alkyl radical, optionally comprising one or more hetero atoms, for example such as oxygen.

Preferably, the radicals R and R$_1$ to R$_4$, which may be identical or different, are chosen from hydrogen, R', —OR', —OCOR' and —COOR' with R' representing a linear or branched C$_1$–C$_6$ alkyl radical, and from the following neutralized or nonneutralized solubilizing groups: —COOH, —CH$_2$COOH, —CH$_2$OH, —(CH$_2$)$_6$OH, —(CH$_2$)$_3$SO$_3$H, —O(CH$_2$)$_3$SO$_3$H, —O(CH$_2$)$_3$N(CH$_2$CH$_3$)$_2$, —[(CH$_2$)$_2$O]$_x$CH$_2$CH$_2$OH, —[(CH$_2$)$_2$O]$_x$CH$_2$CH$_2$OCH$_3$ with x being an average number between 0 and 200.

In accordance with one particular embodiment of the invention, the conductive polymer used comprises at least one solubilizing group per repeating unit.

The conductive polymers present in the composition according to the invention are well known to those skilled in the art and described especially in the book "Handbook of Organic Conductive Molecules and Polymers"—Wiley 1997—New York, Vol. 1, 2, 3, but also in the revue Can. J. Chem. Vol 64, 1986. Polythiophenes and the synthesis thereof are more particularly described in the article taken from the review Chem. Mater. 1998, Vol. 10, No. 7, pages 1990–1999 by the authors Rasmussen S. C., Pickens J. C. and Hutchison J. E. "A new, general approach to tuning the properties of functionalized polythiophenes: The oxidative polymerization of monosubstituted bithiophenes"; in the article taken from the review Macromolecules 1998, 31, pages 933–936, by the same authors "Highly conjugated, water-soluble polymers via direct oxidative polymerization of monosubstituted bithiophenes". Besides polymerization via chemical or electrochemical oxidation, they may also be obtained by polycondensation (dihalogenated thiophene; catalysis with nickel or palladium complexes); by Suzuki coupling (coupling between a halogen function, for example bromine, and a boronic acid, catalysis: complex of palladium and base; this then gives coupling of AA-BB type (reaction of monomers of the type A-X-A with B-X'-B) or of A-B type (reaction of several monomers of A-X-B type)); by Stille coupling (formation of a carbon-carbon bond in the presence of Pd-based catalysis of AA-BB or A-B type); by Reike polymerization (organozinc in the presence of a nickel complex); by McCulloch type polymerization, etc. The conductive polymers present in the composition according to the invention are moreover described in international patent application WO 99/47570.

Among the conductive polymers that are suitable for performing the present invention, mention may be made more particularly of the polymers corresponding to formulae (III) and (IIIbis) in which the solubilizing groups are preferably a carboxylic acid group; a sulfonic acid group; a tertiary amine radical; a quaternary ammonium radical such as —NR'$_3^+$Z$^-$ with Z=Br, Cl or (C$_1$–C$_4$)alkyl-OSO$_3$ and R' alkyl, which may be identical or different, C$_1$ to C$_{20}$ linear or branched, or two of them forming a heterocycle with the nitrogen; said groups optionally being linked to the ring via a spacer. The carboxylic or sulfonic acid functions may or may not be neutralized.

Preferably, the conductive polymer is chosen from those of formulae (III) and (IIIbis) in which at least one radical R$_1$ to R$_4$ of formula (IIIa) or R$_1$ or R$_2$ in formula (IIIb) or (IIIbis) represents a solubilizing group of the carboxylic acid type, in neutralized or nonneutralized form, optionally linked to the ring via a spacer, preferably a linear or branched C$_1$–C$_{20}$ alkyl radical, the other radical(s) representing a hydrogen atom.

The conductive polymers are generally present in the composition in proportions of at least 0.001% by weight, more particularly of at least 0.01% by weight, preferably of at least 0.1% by weight and even more preferably of at least 0.5% by weight, relative to the total weight of the composition. Moreover, the content of conductive polymer is advantageously not more than 50% by weight, more particularly not more than 30% by weight, preferably not more than 20% by weight and even more preferably not more than 10% by weight, relative to the total weight of the composition.

According to a particularly advantageous embodiment of the invention, the content of conductive polymer is between 0.1% and 50% by weight, more preferably between 0.1 and 30% by weight, and preferably between 0.5% and 10% by weight, relative to the total weight of the composition.

Medium

The cosmetically acceptable medium of the cosmetic composition is preferably an aqueous medium consisting of water and may advantageously comprise cosmetically acceptable organic solvents including, more particularly, alcohols such as ethyl alcohol, isopropyl alcohol, benzyl alcohol and phenylethyl alcohol, or glycols or glycol ethers such as, for example, ethylene glycol monomethyl, monoethyl or monobutyl ether, propylene glycol or ethers thereof such as, for example, propylene glycol monomethyl ether, butylene glycol, dipropylene glycol and also diethylene glycol alkyl ethers, for instance diethylene glycol monoethyl ether or monobutyl ether, or alternatively polyols, for instance glycerol. Polyethylene glycols and polypropylene glycol and mixtures of all these compounds may also be used as solvent.

The solvents may then be present in concentrations of between 0.5% and 20% and preferably between 2% to 10% by weight relative to the total weight of the composition.

Additives

The cosmetic composition may also comprise an effective amount of other agents, which are previously known elsewhere in the treatment of human keratin fibers, such as various common adjuvants, for instance surfactants that are well known in the prior art and of anionic, cationic, nonionic, amphoteric or zwitterionic type or mixtures thereof, thickeners, antioxidants, fragrances, dispersants, conditioners especially including cationic or amphoteric polymers, opacifiers, sequestering agents such as EDTA and etidronic acid, UV-screening agents, waxes, volatile or nonvolatile, cyclic or linear or branched silicones, which are organo-modified (especially with amine groups) or unmodified, preserving agents, ceramides, pseudoceramides, plant, mineral or synthetic oils, vitamins or provitamins, for instance panthenol, and nonionic, anionic, amphoteric or cationic associative polymers.

Surfactants

Preferably, the cosmetic composition according to the invention comprises one or more surfactants that may be chosen, without preference, alone or as mixtures, from anionic, amphoteric, nonionic, zwitterionic and cationic surfactants.

The surfactants that are suitable for carrying out the present invention are especially the following:

(i) Anionic Surfactant(s):

As examples of anionic surfactants which can be used, alone or as mixtures, in the context of the present invention, mention may be made in particular (nonlimiting list) of salts (in particular alkaline salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$–$C_{24}$) alkyl sulfosuccinates, ($C_6$–$C_{24}$) alkyl ether sulfosuccinates, ($C_6$–$C_{24}$) alkylamide sulfosuccinates; ($C_6$–$C_{24}$) alkyl sulfoacetates; ($C_6$–$C_{24}$) acyl sarcosinates and ($C_6$–$C_{24}$) acyl glutamates. It is also possible to use the carboxylic esters of ($C_6$–$C_{24}$) alkylpolyglycosides, such as alkylglucoside citrates, alkylpolyglycoside tartrates and alkylpolyglycoside sulfosuccinates, alkylsulfosuccinamates; acyl isethionates and N-acyltaurates, the alkyl or acyl radical of all of these various compounds preferably containing from 12 to 20 carbon atoms, and the aryl radical preferably denoting a phenyl or benzyl group. Among the anionic surfactants which can also be used, mention may also be made of fatty acid salts such as the salts of oleic, ricinoleic, palmitic and stearic acids, coconut oil acid or hydrogenated coconut oil acid; acyl lactylates in which the acyl radical contains 8 to 20 carbon atoms. Alkyl-D-galactosideuronic acids and their salts, polyoxyalkylenated ($C_6$–$C_{24}$) alkyl ether carboxylic acids, polyoxyalkylenated ($C_6$–$C_{24}$) alkylaryl ether carboxylic acids, polyoxyalkylenated ($C_6$–$C_{24}$) alkylamido ether carboxylic acids and their salts, in particular those containing from 2 to 50 alkylene oxide, in particular ethylene oxide, groups, and mixtures thereof can also be used.

(ii) Nonionic Surfactant(s):

The nonionic surfactants are also compounds that are well known per se (see in particular in this respect "Handbook of Surfactants" by M. R. Porter, published by Blackie & Son (Glasgow and London), 1991, pp. 116–178) and, in the context of the present invention, their nature is not a critical feature. Thus, they can be chosen in particular from (nonlimiting list) polyethoxylated or polypropoxylated alkylphenols, α-diols or alcohols having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$–$C_{14}$)alkylamine oxides or N-acylaminopropylmorpholine oxides.

(iii) Amphoteric or Zwitterionic Surfactant(s):

The amphoteric or zwitterionic surfactants, whose nature is not a critical feature in the context of the present invention, can be, in particular (nonlimiting list), aliphatic secondary or tertiary amine derivatives in which the aliphatic radical is a linear or branched chain containing 8 to 18 carbon atoms and containing at least one water-soluble anionic group (for example carboxylate, sulfonate, sulfate, phosphate or phosphonate); mention may also be made of ($C_8$–$C_{20}$)alkylbetaines, sulfobetaines, ($C_8$–$C_{20}$) alkylamido ($C_1$–$C_6$) alkylbetaines or ($C_8$–$C_{20}$) alkylamido ($C_1$–$C_6$) alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names amphocarboxyglycinates and amphocarboxypropionates of respective structures:

$R_2$—$CONHCH_2CH_2$—$N(R_3)$ ($R_4$) ($CH_2COO^-$)

in which: $R_2$ denotes an alkyl radical of an acid $R_2$—COOH present in hydrolyzed coconut oil, a heptyl, nonyl or undecyl radical, $R_3$ denotes a β-hydroxyethyl group and $R_4$ denotes a carboxymethyl group; and $R_2'$—$CONHCH_2CH_2$—$N(B)$ (C)

in which:

B represents —$CH_2CH_2OX'$, C represents —$(CH_2)_z$—Y', with z=1 or 2,

X' denotes a —$CH_2CH_2$—COOH group or a hydrogen atom,

Y' denotes —COOH or a —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium coco-ampho-diacetate, disodium lauro-ampho-diacetate, disodium capryl-ampho-diacetate, disodium caprylo-ampho-diacetate, disodium coco-ampho-dipropionate, disodium lauro-ampho-dipropionate, disodium capryl-ampho-dipropionate, disodium caprylo-ampho-dipropionate, lauro-ampho-dipropionic acid and coco-ampho-dipropionic acid.

By way of example, mention may be made of the coco-amphodiacetate sold under the trade name Miranol® C2M Concentrate by the company Rhodia Chimie.

(iv) Cationic Surfactants:

Among the cationic surfactants that may be mentioned in particular (nonlimiting list) are: primary, secondary or tertiary fatty amine salts, optionally polyoxyalkylenated; quaternary ammonium salts such as tetraalkylammonium, alkylamidoalkyl-trialkylammonium, trialkylbenzylammonium, trialkylhydroxyalkylammonium or alkylpyridinium chlorides or bromides; imidazoline derivatives; or amine oxides of cationic nature.

The amount of surfactants present in the composition according to the invention may range from 0.01 to 40% by weight and preferably from 0.5 to 30% by weight, relative to the total weight of the composition.

Needless to say, a person skilled in the art will take care to select the optional additional compound(s) mentioned above, such that the advantageous properties intrinsically associated with the dye composition according to the invention are not, or are not substantially, adversely affected by the envisaged addition(s).

The composition which has just been described is generally applied to wet or dry keratin fibers. The composition medium is then evaporated, or left to evaporate at between 20 and 120° C., preferably between 20 and 80° C. until the fibers are dry. It is also possible to apply the composition to wet or dry fibers, and then to rinse said fibers and dry them at between 20 and 120° C.

The invention makes it possible to produce a visual effect which is more particularly a sheen effect of the keratin fibers treated.

This visual effect may also be a color effect when the conductive polymer absorbs in the visible spectrum.

The examples which follow illustrate the invention without, however, being limiting in nature.

EXAMPLE 1

Synthesis of poly(3-thiopheneacetic acid)

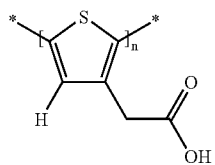

Procedure

Preparation of the Polymer: poly(ethyl 3-thiopheneacetate)

25 ml of dry chloroform are introduced into a Schlenk tube under argon, the system is degassed and the following reagents are then introduced:

2.5 g of ethyl 3-thiopheneacetate (14.7 mmol)

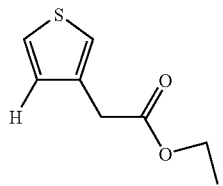

and 1 g of $FeCl_3$ (6.15 mmol).

The mixture is stirred for 24 hours under argon at 50° C.

The polymer poly(ethyl 3-thiopheneacetate) is then precipitated from heptane.

The polymer is then dissolved in a tetrahydrofuran solution.

Characterization by Infrared:

C=O band: 1 719 $cm^{-1}$; $CH_2$ and $CH_3$ bands=2 979 $cm^{-1}$, 2 934 $cm^{-1}$ and disappearance of the CH band at 3 102 $cm^{-1}$ present in the monomer.

Hydrolysis of the Polymer: poly(ethyl 3-thiopheneacetate) to Form poly(3-thiopheneacetic acid).

The polymer obtained above is then hydrolyzed with an excess of 50 ml of aqueous sodium hydroxide solution (2N) for 48 hours at 70° C., followed by acidification with concentrated HCl to the point of precipitation of the product: poly(3-thiopheneacetic acid).

The polymer is then filtered off and washed several times with distilled water in order to remove the traces of catalyst.

Infra-red Characterization of the Polymer:

C=O band: 1 740 $cm^{-1}$; COO 1 580 $cm^{-1}$; OH (broad band 3 000–3 500 $cm^{-1}$)

Neutralization of the Polymer poly(3-thiopheneacetic acid):

The polymer poly(3-thiopheneacetic acid) (2 g) is dissolved in tetrahydrofuran (30 g) and neutralized at a rate of 1 mol of sodium hydroxide per mole of carboxylic acid. Water (30 g) is then added.

The tetrahydrofuran is evaporated off.

An aqueous 6% solution of poly(3-thiophene-acetic acid) in the form of a sodium salt is thus obtained.

Formulation Comprising the Polymer Obtained:

| Composition: | |
| --- | --- |
| Polymer obtained above | 4% |
| Aminomethylpropanol | qs pH 7 |
| Synthalen K | 1% |
| Ethanol | 10% |
| Water | qs 100 g |

The composition described above, comprising the conductive polymer obtained according to the preceding example, is applied to locks of natural chestnut-brown hair at room temperature (20° C.) (0.1 g per g of hair). The locks are then dried.

The locks have a very shiny appearance with a golden glint, which is especially perceptible when the locks are observed at a low angle.

To the touch, the hair has the advantage of not being perceived as greasy, the optical properties described above being maintained over time (unchanged after 12 hours).

EXAMPLE 2

The preceding example is reproduced, except that the polymer obtained is neutralized with triethylamine instead of sodium hydroxide.

What is claimed is:

1. A composition for dyeing human keratin fibers comprising a cosmetically acceptable medium and, in said medium, an effective amount of at least one conductive polymer chosen from:

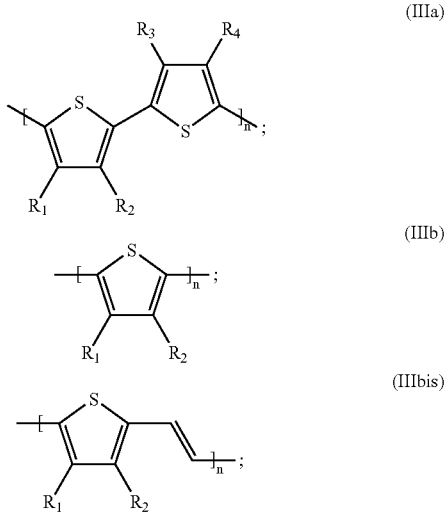

where:
n ranges from 5 to 10,000;
$R_1$, $R_2$, $R_3$, and $R_4$, which may be identical or different, are chosen from hydrogen, —R', —OR', —COOR', —OCOR', a halogen atom, a nitro radical, a cyano radical, an alkylcyano radical, a solubilizing group, and a spacer-linked solubilizing group;
R' is chosen from a linear or branched $C_1$–$C_{20}$ alkyl radical;
at least one of $R_1$, $R_2$, $R_3$, and $R_4$ is chosen from a solubilizing group and a spacer-linked solubilizing group;
the spacer-linked solubilizing group comprises a spacer group and at least one solubilizing group where the spacer group links to the ring the at least one solubilizing group;
and the at least one conductive polymer is in soluble form and absorbs in the visible spectrum,
wherein the at least one conductive polymer is present at a concentration of at least 0.001% by weight relative to the total weight of the composition.

2. The composition of claim 1 wherein n ranges from 20 to 700.

3. The composition of claim 1 wherein the spacer group is chosen from —R"—, —OR"—, —OCOR"—, and —COOR"—;
where R" is a linear or branched $C_1$–$C_{20}$ alkyl radical optionally comprising at least one hetero atom.

4. The composition of claim 3 wherein the at least one hetero atom is chosen from oxygen and nitrogen.

5. The composition of claim 1, wherein the at least one solubilizing group is chosen from —COOH, —COO$^-$M$^+$, —SO$_3$H, —SO$_3^{-M+}$, a primary amine radical, a secondary amine radical, a tertiary amine radical, a quaternary ammonium radical, a hydroxyl radical, and a $C_2$–$C_3$ polyalkene oxide radical;
where:
M is chosen from an alkali metal, an alkaline-earth metal, an organic amine, an alkanolamine and an amino acid.

6. The composition of claim 5 wherein the quaternary ammonium radical is —NR'$_3^+$Z$^-$;
where:
Z is chosen from Br, Cl, and ($C_1$–$C_4$)alkyl-OSO$_3$;
R' are linear or branched $C_1$ to $C_{20}$ alkyls which may be identical or different; and
two of R' alkyls optionally form a heterocycle with the nitrogen.

7. The composition of claim 1 wherein the conductive polymer comprises at least one solubilizing group per repeating unit.

8. The composition of claim 1 wherein the at least one conductive polymer is chosen from formula (IIIa), formula (IIIb) and formula (IIIbis);
where:
if formula (IIIa) is chosen then at least one of $R_1$, $R_2$, $R_3$, and $R_4$ are chosen from a solubilizing group and a spacer-linked solubilizing group;
if formula (IIIb) is chosen then at least one of $R_1$ and $R_2$ are chosen from a solubilizing group and a spacer-linked solubilizing group;
if formula (IIIbis) is chosen then at least one of $R_1$ and $R_2$ are chosen from a solubilizing group and a spacer-linked solubilizing group;
the solubilizing group or the at least one solubilizing group attached to the spacer-linked solubilizing group is chosen from —COOH and COO$^-$M$^+$ where M is chosen from an alkali metal, an alkaline-earth metal, an organic amine, an alkanolamine and an amino acid; and
the radicals that are not solubilizing groups or spacer-linked solubilizing groups are hydrogen atoms.

9. The composition of claim 8 wherein the spacer group of the spacer-linked solubilizing group is chosen from linear $C_1$–$C_{20}$ alkyl radicals and branched $C_1$–$C_{20}$ alkyl radicals.

10. The composition of claim 1 wherein the at least one conductive polymer is present at a concentration of at least 0.5% by weight relative to the total weight of the composition.

11. The composition of claim 1 wherein the at least one conductive polymer is present at a concentration ranging from 0.001% to 50% by weight relative to the total weight of the composition.

12. The composition of claim 1 wherein the at least one conductive polymer is present at a concentration ranging from 0.001% to 10% by weight relative to the total weight of the composition.

13. The composition of claim 1 wherein the composition further comprises water or a water/solvent mixture.

14. The composition of claim 13 wherein the solvent is chosen from alcohols, glycols, glycol ethers, polyols, polyethylene glycols and polypropylene glycol, and mixtures thereof.

15. The composition of claim 1 wherein the composition further comprises at least one surfactant chosen from nonionic surfactants, anionic surfactants, cationic surfactants, amphoteric surfactants, and zwitterionic surfactants.

16. The composition of claim 1 wherein the human keratin fibers are human hair.

17. The composition of claim 1 wherein the at least one conductive polymer has a conductivity ranging from $10^{-5}$ to $5\times10^5$ siemens/cm.

18. The composition of claim 1 wherein the at least one conductive polymer has a conductivity ranging from $10^{-1}$ to $10^4$ siemens/cm.

* * * * *

UNITED STATES PATENT AND TRADEMARK OFFICE
CERTIFICATE OF CORRECTION

| | |
|---|---|
| PATENT NO. | : 7,217,295 B2 |
| APPLICATION NO. | : 10/355227 |
| DATED | : May 15, 2007 |
| INVENTOR(S) | : Henri Samain et al. |

Page 1 of 1

It is certified that error appears in the above-identified patent and that said Letters Patent is hereby corrected as shown below:

Column 13, line 67, "-SO$_3^{-M+}$," should read -- -SO$_3^-$M$^+$,--.

Column 14, line 36, "COO$^-$M$^+$" should read -- -COO$^-$M$^+$--.

Signed and Sealed this

Seventeenth Day of July, 2007

JON W. DUDAS
*Director of the United States Patent and Trademark Office*